United States Patent [19]

Campbell et al.

[11] Patent Number: 4,867,982
[45] Date of Patent: * Sep. 19, 1989

[54] TRANSDERMAL DRUG DELIVERY DEVICE

[75] Inventors: Patricia S. Campbell, Palo Alto; James B. Eckenhoff, Los Altos, both of Calif.; Virgil A. Place, Kawaihae, Hi.

[73] Assignee: ALZA Corporation, Palo Alto, Calif.

[*] Notice: The portion of the term of this patent subsequent to Feb. 16, 2005 has been disclaimed.

[21] Appl. No.: 148,417

[22] Filed: Jan. 26, 1988

Related U.S. Application Data

[63] Continuation of Ser. No. 818,561, Jan. 13, 1986, Pat. No. 4,725,439, which is a continuation-in-part of Ser. No. 626,095, Jun. 29, 1984, Pat. No. 4,704,282.

[51] Int. Cl.[4] .................... A61K 9/70; A61K 13/405; A61L 15/03
[52] U.S. Cl. .......................... 424/449; 424/DIG. 14; 424/447
[58] Field of Search ............... 424/449, DIG. 14, 447; 604/897

[56] References Cited

U.S. PATENT DOCUMENTS 4,379,454  4/1983  Campbell et al. ................... 424/449
4,704,282  11/1987 Campbell et al. ................... 424/449
4,725,439  2/1988  Campbell et al. ................... 424/449

Primary Examiner—Ronald W. Griffin
Attorney, Agent, or Firm—Steven F. Stone; Edward L. Mandell; Paul L. Sabatine

[57] ABSTRACT

A medical device for the transdermal delivery of an active agent through sensitive intact skin is provided. The device comprises a matrix containing the drug having reinforcing means, preferably in the form of a fabric, embedded in the upper surface of the matrix. The matrix is formed of an agent permeable material which is tacky but does not adhesively bond to the skin. The device is sufficiently flexible and deformable that the combination of tackiness, flexibility, and deformation permits the device to be maintained in agent transmitting relationship upon skin at such sensitive areas as the scrotum, labia, breast, or penis, for example. In certain embodiments, the skin distal surface is provided with a layer of an agent impermeable material to reduce transfer of the agent from the patient to others.

39 Claims, 2 Drawing Sheets

□ EXAMPLE 1
○ EXAMPLE 2
△ 4 SYSTEMS EXAMPLE 2 ON THIGH

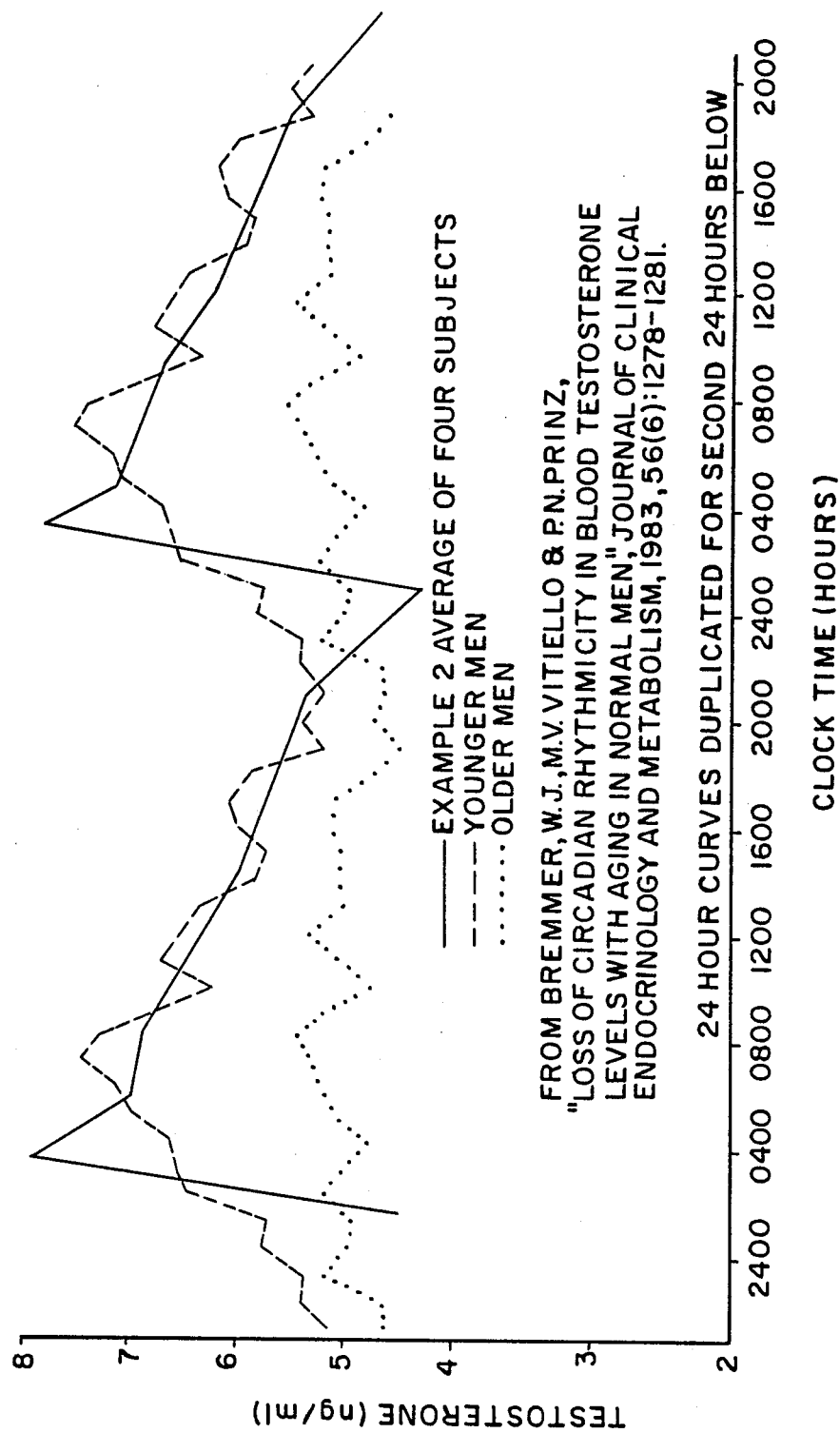

TRANSDERMAL DRUG DELIVERY DEVICE

This application is a continuation of application Ser. No. 06/818,561, filed 01/13/86, now U.S. Pat. No. 4,725,439, which is a continuation-in-part of application Ser. No. 06/626,095, now U.S. Pat. No. 4,704,282.

FIELD OF THE INVENTION

This invention relates to the parenteral delivery of biologically active materials and more particularly to the delivery of such materials to the human body in therapeutic amounts through sensitive areas of intact skin.

BACKGROUND OF THE INVENTION

Certain drugs and other agents are known to be capable of being topically administered to the skin to produce a local or systemic effect upon absorption into the skin. (As used herein, the term "agent" is employed in its broadest sense and applies to any drug or other substance which is delivered to the body to produce a desired, usually beneficial, effect on the recipient.) Originally this was accomplished by application of creams, ointments, gels, solutions or suspensions of the agent in a suitable carrier. This mode of application did not permit precise control of the dose of rate of administration because the amount of agent applied and the surface area covered were highly variable. Accordingly, transdermal delivery devices which deliver known amounts of drug to controlled areas of skin were developed. Representative devices are shown in U.S. Pat. Nos. are 3,249,109, 3,598,122, 4,144,317, 4,201,211, 4,262,003, 4,307,717, and 4,379,454, for example, which patents are incorporated herein by reference. The simplest type of a transdermal delivery device is an agent reservoir of predetermined size and composition, usually a matrix material containing dissolved or dispersed agent, maintained on a predetermined area of the skin for a predetermined period of time by adhesive or other means. Such matrix systems have the advantage of being easily fabricated and are generally of lower cost than more sophisticated rate controlled systems, although the rate of release of an agent from a simple matrix tends to decrease as a function of the time of use.

The site of administration of transdermal delivery devices have been selected at various locations such as behind the ear, on the chest or on the thigh for various reasons such as desired skin permeability to an agent, convenience or cosmetic reasons. It has been known for some time that permeability of human skin varies from site to site and that for certain agents scrotal skin tends to have a higher permability than other skin. Prior to our invention however the only means by which agents were administered through intact scrotal skin was by application of an ointment, cream gel or solution of the agent and we were unaware of any delivery device suitable for transcrotal drug delivery. This was because the shape, texture, environment and sensitivity of the scrotum presented a combination of conditions which were incompatible with the application of prior art delivery devices and the maintenance of such a device in place for an extended time period without discomfort or other adverse side effects.

For example, we have found that the shape and texture of scrotal skin requires a highly flexible device possessing a certain amount of compliance or non-elastic stretch in order to be capable of comfortably conforming to the wrinkles, folds and irregular shape of scrotal skin in agent transmitting relationship thereto and thereafter remain in this slightly deformed condition rather than returning to its original configuration. Patient discomfort is a crucial factor in patient compliance and we have found that comfort depends not only on flexibility and stretchability but also on the texture of the device and the sensations attendant to removal. Typical contact adhesives, belts, buckles and elastic bands were all found to be unacceptably uncomfortable.

According to our invention we have devised a transdermal delivery device which is particularly adapted for the topical and systemic administration of agents to the skin at sensitive body sites such as the scrotum, labia, penis or underside of the breast, for example, for which heretofore there have been no suitable agent delivery platforms. Typical agents, by way of non-limiting examples, include androgens such as testosterone, estrogens such as estradiol, progestins such a progesterone, steroids such as hydrocortisone and cyproterone, peptides such as LHRH and interferon, and antiviral agents such as acyclovir and phenolphthalein. As used herein, the identification of an agent to be delivered includes not only the compound per se but also its topically administrable prodrugs, active metabolites and prodrugs of the active metabolites. Thus for example the reference to testosterone includes testosterone per se, its prodrugs such as testosterone enanthate, its active metabolite, dihydrotestosterone and its prodrug dihydrotestosterone enanthate, for example.

According to an embodiment of this invention, agent release through the body distal surface of this device is substantially reduced without adversely affecting the texture, flexibility, stretchability or tack.

Accordingly, it is an object of this invention to provide an agent delivery device particularly adapted for scrotal delivery of drugs and other agents through intact scrotal skin.

It is another object of this invention to provide a platform for agent delivery suitable for use on sensitive body sites such as the scrotum, labia, penis and breast.

It is another object of this invention or provide a simple, inexpensive transdermal agent delivery device particularly suited for delivering agents through sensitive body surfaces.

It is another object of this invention to deliver testosterone to a hypogonadal patient in a manner which produces blood levels which simulate normal daily blood level fluctuations.

It is another object of this invention to treat sexual dysfunction by transcrotal delivery of testosterone to obtain both a physiological and a psychological effect.

These and other objects of the invention will be readily apparent from the following description with reference to the accompanying drawings wherein:

FIG. 3 is a plot of in vivo blood levels vs time comparing normal levels with those obtained from embodiments of this invention on hypogonadal males.

DESCRIPTION OF THE INVENTION

Figure 1:
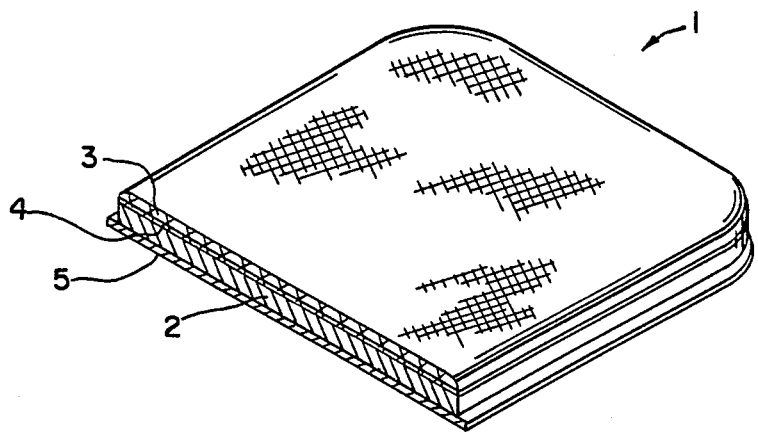
FIG. 1 represents a cross-section through a perspective view of one embodiment on this invention.

An agent delivery device 1 according to this invention is shown in FIG. 1. Such a device 1 comprises a reservoir 2 in the form of a non-aqueous polymeric carrier having the agent to be delivered dissolved or dispersed therein, which carrier has a viscosity and strength sufficient to enable the device to maintain its structural integrity during use without oozing, flowing or otherwise disintegrating. In addition, the reservoir has a limited amount of tack to permit it to cling to the skin to which it is applied without actually being adhesively bonded thereto. The carrier may optionally contain skin permeation enhancers, stabilizing agents, or other additives as is known to the art.

In order to strengthen the reservoir 2, facilitate handling, application and removal of the device and to provide a textured feel to the body distal portion of the device 1, the body distal surface is provided with reinforcing means 3, typically in the form of a nonwoven, woven or knit, relatively open mesh fabric, chemically inert with respect to other components of the system. An impermeable release liner 5, adapted to the easily removed from the body contacting surface of the drug reservoir 2 prior to use would normally be provided to protect the system in its package.

Reinforcing means 3 is bonded to the device, embedded either in the upper surface of reservoir 2 or, in a preferred embodiment, in a discrete layer of bonding agent 4 having characteristics different from those of the carrier forming reservoir 2.

The device of this invention must be sufficiently flexible and compliant to closely conform to the scrotal or other skin and to be maintained in agent transmitting contact without adhesive bonding. This is accomplished by a combination of flexibility, compliance and the non-adhesive tack of the reservoir as hereafter described in detail.

Suitable carriers for the fabrication of the reservoir can be selected from a wide variety of materials known to the art, provided they possess the required compatibility with the agent, structural strength, flexibility and tackiness required. As noted in the U.S. Patents cited above, such materials include, without limitation, tacky natural and synthetic polymers and blends such as natural or synthetic rubbers, and ethylene vinylacetate (EVA) copolymers such as are disclosed for example in U.S. Pat. Nos. 4,069,307 and 4,144,317 which as incorporated herein by reference. EVA polymers having a VA content of from about 28-61% and preferably about 40-60% possess characteristics of solubility, permeability and tack to be suitable for the delivery of a wide variety of agents according to this invention.

Although any agent which is suitable for transdermal administration can be delivered according to this invention certain agents are particularly suited for administration from devices according to this invention. Testosterone constitutes a preferred agent according to this invention, particularly for use in treatment of hypogonadal males. Embodiments of our invention are capable of producing testosterone blood levels which exhibit a pattern more closely approximating the normal circadian hormone pattern via transcrotal administration than are obtained by application to sites other than the scrotum.

Other preferred agents include estradiol, which can be administered to the labia for treatment of post menopausal disorder for example and progesterone which can be administered to the breast to correct oestrogen-progesterone imbalance in women with benign breast disease as suggested by J. De Boever et al., *Variation of Progesterone,* 20 α-Dihydroprogesterone and Oestradiol Concentration in *Human Mammary Tissue and Blood After Topical Administration of Progesterone,* Percutaneous Absorption of Steroids, Academic Press, New York, pp. 259–265 (1980) and R. Sitruk-Ware et al., *Treatment of Benign Breast Diseases by Progesterone Applied Topically,* Ibid. pp. 219–229.

Anti-viral agents, particularly for treating herpes, such as interferon, acyclovir or phenolphthalein as disclosed in U.S. Pat. No. 4,256,763 which is incorporated herein by reference may also be administered according to this invention.

Antiandrogens which have known utility in treatment of prostatic cancer as well as application as contraceptives are also particularly suitable. Cyproterone acetate either alone or with LHRH can be administered according to this invention and thereby avoid the 90–95% first-pass metabolism encountered through oral administration.

The initial loading of agent in the carrier will determine the useful life of the device, useful lives of from about 8 hours to 1 week being typical for transdermal devices generally. This invention can be used for such time periods, however, certain preferred embodiments are particularly adapted for administration periods of up to about 24 hours. The concentration of the agent in the carrier can vary over relatively wide limits, the maximum concentration being determined by the amount of agent that can be received in the carrier without producing adverse histological effects such as irritation, an unacceptably high initial pulse of agent into the body or adverse effects on the characteristics of the device such as loss of tackiness, viscosity or deterioration of other properties. If the device contains agent in an amount in excess of saturation, the excess will function as a unit activity source until depleted. If subsaturated systems are employed, the release rate will tend to decrease more rapidly with time of use than with saturated systems. This characteristic is particularly useful with hormones such as testosterone in which a circadian variation in blood level is normal. With respect to certain specific embodiments, we have found it desirable to maintain the agent concentration below that level at which the agent crystallizes to prevent loss of tackiness.

Suitable reinforcing means 3 include spun bonded polyester and polyamide fabrics such as noted above as well as natural or synthetic woven or knit fabrics, and chopped rovings which may, in certain embodiments, be made from, or be coated with a material having the solubility characteristics for a particular agent and matrix with respect to which it is incorporated, as disclosed and claimed in our copending U.S. patent application Ser. No. 626,095.

The reinforcing means are preferably incorporated as stretchable, typically spun-bonded, fabrics consisting of either randomly oriented bonded fibers which form an isotropic web equally deformable in all directions or an anisotropic web formed from a multiplicity of continuous generally parallel fibers having randomly oriented fibers bonded transversely thereto which is deformable primarily in the direction perpendicular to the continuous fibers. Woven and knit fabrics can also be used. These fabrics tend to curl when the release liner is removed and are preferably applied in a manner in which the curl tends to envelop the scrotum rather then separate therefrom to assist in maintaining contact.

The reinforcing means 3 can be embedded in the upper surface of the reservoir 2 or may be embedded in the upper surface of a layer of bonding agent 4 which is applied over reservoir 2. The reinforcing means is preferably not totally submerged in the material in which it is embedded so that the skin distal surface of the device retains a textured feel rather than presenting a smooth surface. By embedding the reinforcement means 3 in a bonding agent formed of a material different from the carrier, it is possible to use a bonding material which is substantially impermeable to the drug to be delivered and thereby reduce the amount of agent that can be released through the skin distal surface. The bonding agent should be selected to be adherent to both the matrix material and the reinforcement means and be relatively impermeable to the agent to be delivered. Polyisobutylene (PIB) and silicone adhesives, for example, are useful for many combinations of materials. In transcrotal delivery of testosterone, for example, release of testosterone to a female sexual partner could be undesirable. This embodiment of our invention provides an integral impermeable barrier without impairing the textured feel or other characteristics of the skin distal surface of the device.

Delivery devices according to this invention normally comprise devices having a surface area in the range of from about 15–75 cm$^2$, depending on site of application. Smaller systems have a tendency to fall off prematurely and larger systems may be too large for the average penis, scrotum, labia or breast. The preferred range is about 20–60 cm$^2$, a typical transcrotal device being fabricated as an approximately 40 cm$^2$ generally rectangular patch with rounded corners. The patches are intended to be applied and left in place preferably while wearing close fitting clothing such as jock strap or jockey shorts, panties or brassiere for example to protect the device from unnecessary physical contact or motion and assist in maintaining the device in contact with the skin, for the desired time period. When applied to the penis or breast, the devices would be configured appropriately for their environment of use as elongated strips or kidney shaped devices respectively.

The sensitivity of scrotal, penile, labial, and mammary skin and their sometimes irregular and changing configurations imposes significant constraints on the characteristics of a delivery device according to this invention. For example, the device must be both sufficiently thin, flexible and stretchable so as to easily conform to the configuration of the site of application and have sufficient nonadhesive tack to stay in skin contact in a manner which does not create discomfort on removal. The requires combination of characteristics can be obtained from devices having a thickness in a range from approximately 2 to 10 mil with approximately 3 to 5 mil being preferred.

The non-adhesive tack of the skin contacting surface should be sufficiently high to maintain contact during use and sufficiently low to be removable without pain, discomfort or irritation. Peel strength from skin in the range of 1–20 gm/cm were contemplated but this value is extremely difficult to measure accurately or reproducibly. Accordingly, the properties possessed by the devices of this invention have been quantitified by test procedures which are accurate and reproducible in vitro.

A Polykon Digital Probe Tack Tester, Model #80-20-01 was used to quantify the tack possessed by devices according to this invention. In the test procedure the probe of the Tack Tester is forced into the surface to be tested at 35° C. with a contact pressure of 500 g/cm$^2$ for 10 seconds and thereafter withdrawn from the surface at a rate of 1 cm/sec. The maximum force exerted before the probe releases from the surface is recorded. The maximum and minimum tack values for devices according to this invention are in the range of from about 50–500 g/cm$^2$ with optimum values being about 100–300 g/cm$^2$. Tack values referred to hereinafter are determined by this test.

In addition to the tack of the body contacting surface, the device of this invention also possesses certain required characteristics of modulus, stress decay and elongation in at least one dimension when measured at room temperature (approximately 20° C.). When anisotropic reinforcing means are employed, the following characteristics apply to deformation along the weakest axis. The device should have an extension modulus at 15% extension in the range of 1000–15,000 g/cm$^2$ and preferably 1000–5000 g/cm$^2$. It should also possess a stress decay in the range of about 25% to 45% within 5 minutes after a 15% extension. In addition a 2 cm wide strip of this device should require an elongation force of from about 30–300 gm and preferably 50–150 gm to produce a 15% extension of the device.

The above characteristics of the device can be obtained by appropriate combination of the materials forming the reinforcing means and the reservoir if these materials have certain characteristics.

The reinforcing means should have a modulus at 15% extension of from about 800 to 60,000 g/cm$^2$ and preferably 1500–15,000 gm/cm$^2$ with stress decay from about 30–45% in 5 minutes after a 15% elongation. In the event a bonding layer is incorporated, the bonding layer is preferably selected from a material that, at the thickness used, does not cause the modulus or stress relaxation of the reinforcing means/bonding agent composite to vary by more than about 5% from that of the reinforcing means alone.

The reservoir should have an extension modulus significantly lower than that of the reinforcing means, typically less than 1500 g/cm$^2$ and preferably in the range of about 800–1200 g/cm$^2$; a stress decay of less than 25% and preferably from about 10–20% in 5 minutes at 15% extension.

Having thus generally described our invention, the following examples are provided.

EXAMPLE 1

A spun-bonded polyester fabric, 0.3 oz/yd$^2$ (equivalent to 1 mg/cm$^2$) sold by Chicopee Mills as Fabric Code No. 9123, was laid upon a release surface of an impermeable silicone-coated polyester film and a 50/50 mixture of low average molecular weight (35,000) and high average molecular weight (1,200,000) polyisobutylene (PIB) in heptane was cast onto the fabric at a loading of 1 mg PIB/cm$^2$. Upon evaporation of the heptane, the upper surface of the fabric was sufficiently exposed to have a distinct textured feel with the PIB concentrated in the lower portion of the fabric at a thickness of about 0.4 mils.

A mixture of 2 wt % testosterone and 98 wt % EVA (40% VA) was dissolved in methylene chloride and cast onto a fluorocarbon coated polyester release liner available from 3M Co. to produce, after evaporation of the solvent, a reservoir loading of 12.5 mg/cm$^2$ containing 0.25 mg testosterone per cm$^2$. The spun bonded polyester/PIB laminate was removed from its release liner and the PIB surface was laminated and bonded to the testosterone reservoir at 90° C.

When the resultant product is die cut into 20 cm$^2$, 40 cm$^2$ and 60 cm$^2$ rectangles with rounded corners it provides systems having testosterone loadings of 5, 10 and 15 mg respectively. These devices are suitable for the transcrotal administration of testosterone. The tack of the systems was about 100 g/cm$^2$, the elongation modulus was 1670 g/cm$^2$, the stress decay was 33% and the elongation force was 55 gm. Those systems should be stored above about 23° C. to prevent crystallization of testosterone which resulted in some loss of tack

EXAMPLE 2

24.38 parts EVA (51% VA) were dissolved in 75.62 parts methylene chloride to which was added 0.625 parts testosterone and mixed until dissolution occurred. The solution was then solvent cast as a 3.5 mil film onto an impermeable silicone/polyester release liner and the solvent evaporated to yield a material comprising 97.5% EVA and 2.5% testosterone. A spun bond polyester fabric, 0.5 oz/yd$^2$, sold by Chicopee Mills as fabric Code No. 9123 was applied over the approximately 3.5 ml thick EVA layer. The test sample was thereafter die cut into a rectangular shape with rounded corners approximately 5×7 cm in each major dimension, in the process of which the spun bond polyester fabric was embedded in the upper surface of the EVA layer. The device had a tack of 250 gm/cm$^2$, an elongation modulus of 4100, gm/cm$^2$, a stress decay of 38% and an elongation force of 104 gm.

EXAMPLE 3

Figure 2:
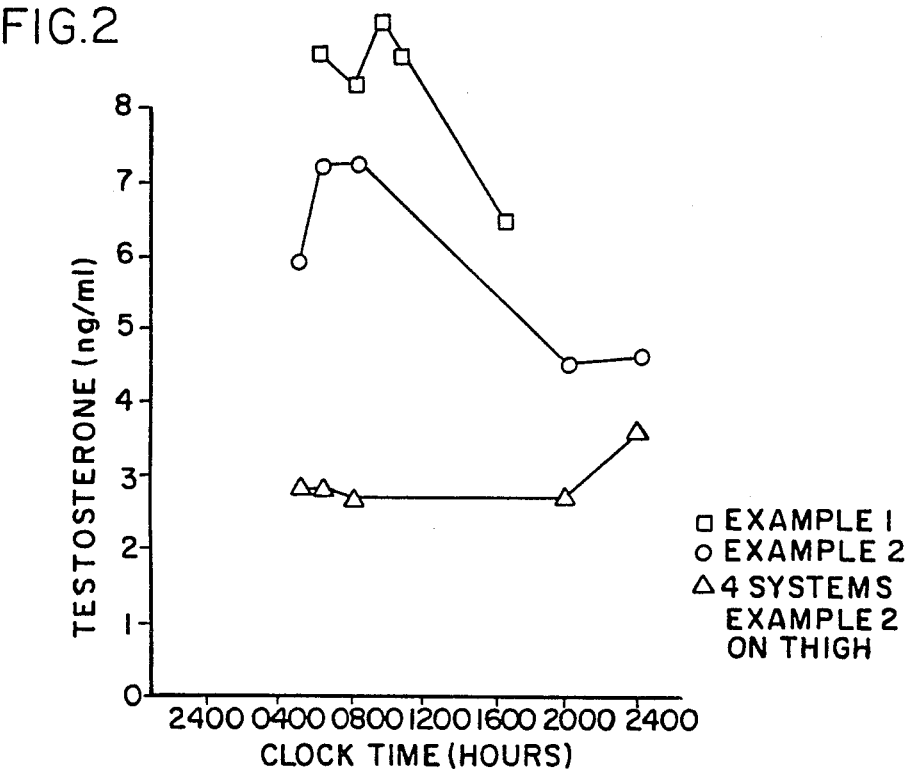
FIG. 2 is a plot of in vivo testosterone blood levels obtained from embodiments of the invention applied to the scrotum and the thigh.

After removal of the impermeable release liner, transcrotal delivery devices produced according to Examples 1 and 2 may be applied to the scrotum of a testosterone deficient male prior to retiring or in the morning and left in place for between 8 and 24 hours depending on the cyclical testosterone blood levels desired for testosterone replacement therapy. After initial application new systems may be applied immediately or after a predetermined time interval as a means of chronic therapy. The blood levels obtained from application of such systems to hypogonadal males are shown in FIG. 2. To illustrate the desirability of the scrotum for transdermal testosterone delivery, four of the 35 cm$^2$ systems of Example 2 were applied to the thigh of a hypogonadal male. The blood level so obtained is also shown in FIG. 2. It is apparent that 4 systems applied to the thigh produced ineffective blood levels whereas one system applied to the scrotum approximated the normal daily blood levels.

FIG. 3 shows the average 24 hour blood levels obtained by application of the devices of Example 2 to the scrotum of four hypogonadal males as compared to normal blood levels, with the 24 hour patterns duplicated for the second 24 hour period. This illustrates the ability of the devices of this invention to mimic normal circadian blood testosterone level variations.

EXAMPLE 4

A progesterone loaded system was prepared by the process described in Example 2 with progesterone being substituted for the testosterone. Two of the rectangular 35 cm$^2$ patches were applied to intact scrotal skin of a human subject, 22 days after base line progesterone blood levels were determined. Blood samples were taken and assayed for progesterone content at various times and the results compared to base line levels are shown in Table 1. As can be seen, the blood levels are markedly increased and promptly returned to base line after removal of the device.

TABLE 1

| Date | Time | Progesterone Blood Level (units) |
| --- | --- | --- |
| Day 1 | 8:53 | 34 ng/dl |
| Day 1 | 11:45 | 33 ng/dl |
| Day 23 | 8:15* | 37 ng/dl |
| Day 23 | 10:22 | 156 ng/dl |
| Day 23 | 12:22 | 191 ng/dl |
| Day 23 | 16:09 | 176 ng/dl |
| Day 24 | 7:00** | |
| Day 24 | 8:57 | 53 ng/dl |

*System Applied
**System Removed

EXAMPLE 5

35 cm$^2$ patches having a generally kidney shaped configuration are also fabricated per Example 4. These patches are suitable for application to the underside of the breast and may be placed within the lower portion of a brassiere cup for convenience. Such a device is useful in correcting oestrogen-progesterone imbalance in women having benign breast disease as suggested by Lafay et al., J. Gyn. Obst. Biol. Repr. Procs, 7, pp. 1123–1139 (1978).

EXAMPLE 6

A transdermal therapeutic system containing hydrocortisone is fabricated by solvent casting from methylene chloride in the form of a 10 mil thick Kraton 2104 styrene-butadiene block copolymer available from shell Chemical Company containing 0.27 weight percent of hydrocortisone. Nomex heat-resistant aromatic polyarylamide fiber available from DuPont Chemical Company is pressed into the upper surface of the Kraton film and die cut into 35 sq$^2$ rectangular patches with rounded edges each containing 2.4 mg of hydrocortisone. Equilibrating for at least 48 hours, the devices may be applied to intact scrotal or labial skin for transdermal delivery of hydrocortisone.

EXAMPLES 7–11

Systems for topical application of interferon, acyclovir, cytopreterone acetate, OHRH and phenolphthalein can be fabricated according to the general procedures of examples 1–6 from the formulations in Table 2.

TABLE 2

| Example # | Drug | Drug Loading gm/cm$^2$ | Reinforcing Means | Matrix | Bonding Agent |
| --- | --- | --- | --- | --- | --- |
| 7 | Interferon | 0.20 | spun bonded polyester | hydrophyllic silicone copolymer (Dow Chemical | None |
| 8 | Acyclovir | 0.25 | spun bonded polyester | EVA (40% VA) | PIB |
| 9 | Cyproterone Acetate | 0.30 | spun bonded polyester | EVA (51% VA) | None |
| 10 | LHRH | 0.10 | spun bonded | EVA (40% VA) | Silicone |

TABLE 2-continued

| Example # | Drug | Drug Loading gm/cm$^2$ | Reinforcing Means | Matrix | Bonding Agent |
|---|---|---|---|---|---|
| | | | polyester | | Adhesive Dow-355 |
| 11 | Phenolphthalein | 0.30 | spun bonded nylon | EVA (51% VA) | None |

EXAMPLE 12

When testosterone ointments were used according to the prior art, it had been reported that female sexual partners were experiencing adverse reactions such as increased hair growth as a result of the transfer of testosterone during intercourse. An experiment was performed to compare how much testosterone was transferred from the back side of devices fabricate according to Example 1 with the amount transferred using Percutacrine ointment.

20 cm$^2$ patches produced according to Example 1 were applied to the scrotums of four subjects and left in place for three hours. The patches were removed and the back (skin distal) surface of the patch was rubbed vigorously on the forearm of each subject. The residual testosterone on each scrotum and forearm was recovered by wiping three times with a cotton swab soaked in isopropyl alcohol and thereafter assayed..

0.2 cc Percutacrine ointment was applied to a 20 cm$^2$ gauze pad and applied to the thigh of the same four subjects. After three hours the gauze was removed and the subjects forearm was vigorously rubbed over the site of application. The residual testosterone was recovered from the forearm and thigh of each subject and assayed as described above. The results are shown in Table 3.

TABLE 3

| | DRUG ON ARM AFTER RUBBING THIGH - REMOVED WITH 3 WIPES | | | | RESIDUAL DRUG ON THIGH AFTER RUBBING WITH ARM - REMOVED WITH 3 WIPES | | | |
|---|---|---|---|---|---|---|---|---|
| | (micrograms) | | | | | | | |
| | WIPE # | | | | WIPE # | | | |
| SUBJECT | 1 | 2 | 3 | SUM | 1 | 2 | 3 | SUM |
| 1 | 6.9 | 7.5 | 5.9 | 20.3 | 123.2 | 63.3 | 37.0 | 223.5 |
| 2 | 19.7 | 11.5 | 8.9 | 40.1 | 93.2 | 48.3 | 23.6 | 165.1 |
| 3 | 22.9 | 9.4 | 6.8 | 39.1 | 78.0 | 42.6 | 19.5 | 140.1 |
| AVERAGE | | | | 32.5 | | | | 207.1 |
| | DRUG ON ARM AFTER RUBBING ON SYSTEM BACK REMOVED WITH 3 WIPES: | | | | RESIDUAL DRUG ON SCROTUM AFTER REMOVING SYSTEM REMOVED WITH 3 WIPES: | | | |
| | (micrograms) | | | | | | | |
| SUBJECT | 1 | 1 | 3 | SUM | 1 | 2 | 3 | SUM |
| 1 | 0.1 | NM* | NM | 0.1 | NM | NM | 0.2 | 0.2 |
| 2 | 0.3 | 0.2 | NM | 0.5 | 1.2 | 1.3 | 0.7 | 3.2 |
| 3 | 0.6 | 0.1 | 0.3 | 1.0 | 1.0 | 0.7 | 0.3 | 2.0 |
| 4 | NM | 0.9 | 0.2 | 1.1 | 0.8 | 1.3 | 0.5 | 2.6 |
| AVERAGE | | | | 0.7 | | | | 2.0 |

*NOT MEASURABLE

The results indicate that the device of Example 1 provides a barrier to the transport of testosterone from the back surface thereof. The results also indicate that less residual testosterone remains on scrotal skin than on thigh skin.

This invention has been described with respect to several specific embodiments thereof. Various substitutions and modifications will suggest themselves to workers skilled in the art which can be made without departing from the scope of this invention which is limited only by the following claims; wherein:

We claim:

1. A flexible and compliant medical device for the transdermal administration of testosterone through intact skin at sensitive body locations, said device being from 2-10 mils thick and having an extension modulus at 15% elongation in at least one direction in the range of 1000 to 15,000 gm/cm$^2$, a stress decay from 15% elongation at 5 minutes in the range of 25-45%, a 2 cm wide strip of said device requiring an elongation force of from 30-300 gm to produce said 15% elongation, said device comprising, in combination;

(a) a testosterone reservoir comprisign testosterone dissolved in ethylene/vinyl acetate copolymer having a vinyl acetate content in the range of 40-60%, said reservoir having a body contacting surface through which agent is released to the skin and a body distal surface opposite said body contacting surface, the body contacting surface of said reservoir having a tack in the range of about 100-300 g/cm$^2$ at 35° C.;

(b) fibrous reinforcing means imbedded in said reservoir to a depth that does not penetrate through said body contacting surface and does not submerge said reinforcing means in said reservoir, said imbedded fibrous reinforcing means forming the body distal surface of said device; said fibrous reinforcing means being non-elastically deformable in at least one direction; whereby the body distal surface of said device retains a fibrous texture and said device is capable of non-adhesively clinging to the skin at sensitive body locations in testosterone transmitting relationship thereto.

2. The device of claim 1 wherein said reservoir comprises an ethylene/vinyl acetate copolymer having a vinyl acetate content of about 51%.

3. The device of claim 2 wherein said reinforcing means comprises a spun bonded fabric having a weight of up to about 0.3 oz./sq. yd.

4. The device of claim 1 wherein said reservoir contains up to about 2.5% testosterone.

5. The device of claim 2 wherein said reservoir contains up to about 2.5% testosterone.

6. The device of claim 1 wherein said device is free of undissolved testosterone and contains testosterone at a loading of from about 5–15 mg.

7. The device of claim 3 wherein said device is free of undissolved testosterone and contains testosterone at a loading of from about 5–15 mg.

8. The device of claim 1 wherein said reservoir comprises an ethylene/vinyl acetate copolymer having a vinyl acetate content of about 40%.

9. The device of claim 8 wherein said reinforcing means comprises a spun bonded fabric having a weight of up to about 0.3 oz./sq. yd.

10. The device of claim 8 wherein said reservoir contains up to about 2.5% testosterone.

11. The device of claim 9 wherein said reservoir contains up to about 2.5% testosterone.

12. The device of claim 9 wherein said device is free of undissolved testosterone and contains testosterone at a loading of from about 5–15 mg.

13. A method for testosterone replacement in hypogonadal males which comprises applying a device according to claim 1 to the genitalia of a hypogonadal male and maintaining said device in testosterone transmitting relationship thereto for at least about 8 hours.

14. The method of claim 13 wherein said device is replaced with a fresh device on a daily basis for so long as testosterone replacement is desired.

15. A method for testosterone replacement in hypogonadic males which comprises applying the device of claim 1 to the scrotum of a hypogonadic male and maintaining said system in testosterone transferring relationship to said scrotum for a least about 8 hours.

16. The method of claim 15 wherein said system is maintained in place for up to about 24 hours and is replaced with a fresh device on a daily basis for so long as testosterone replacement is desired.

17. A method for testosterone replacement in hypogonadal males which comprises applying a device according to claim 1 to the genitalia of a hypogonadal male and maintaining said device in testosterone transmitting relationship thereto for a least about 8 hours.

18. The method of claim 17 wherein said device is replaced with a fresh device on a daily basis for so long as testosterone replacement is desired.

19. A method for testosterone replacement in hypogonadic males which comprises applying the device of claim 7 to the scrotum of a hypogonadic male and maintaining said system in testosterone transferring relationship to said scrotum for at least about 8 hours.

20. The method of claim 19 wherein said system is maintained in place for up to about 24 hours and is replaced with a fresh device on a daily basis for so long as testosterone replacement is desired.

21. A method for testosterone replacement in hypogonadal males which comprises applying a device according to claim 12 to the genitalia of a hypogonadal male and maintaining said device in testosterone transmitting relationship thereto for at least about 8 hours.

22. The method of claim 21 wherein said device is replaced with a fresh device on a daily basis for so long as testosterone replacement is desired.

23. A method for testosterone replacement in hypogonadic males which comprises applying the device of claim 12 to the scrotum of a hypogonadic male and maintaining said system in testosterone transferring relationship to said scrotum for at least about 8 hours.

24. The method of claim 23 wherein said system is maintained in place for up to about 24 hours and is replaced with a fresh device on a daily basis for so long as testosterone replacement is desired.

25. A method for testosterone replacement in human males which comprises applying a testosterone releasing delivery device comprising a testosterone containing polymeric matrix to the male genitalia and maintaining said device in testosterone transmitting relationship thereto for a least about 8 hours.

26. The method of claim 25 further comprising the steps of removing the used device and replacing it with a fresh device on a daily basis for so long as testosterone replacement is desired.

27. A method for testosterone replacement in human males which comprises applying a testosterone releasing delivery device comprising a testosterone containing polymeric matrix to the scrotum and maintaining said device in testosterone transmitting relationship thereto for a least about 8 hours.

28. A method for testosterone replacement in the human male which comprises applying a stretchable testosterone releasing delivery device to the male genitalia by non-elastically stretching the delivery device about the genitalia whereby the device conforms to and clings to the skin of the genitalia and maintaining said device in testosterone transmitting relationship thereto for a least 8 hours.

29. The method of claim 28 wherein the site of administration is the scrotum.

30. The method of claim 28 wherein the body contacting surface of said delivery device has a tack in the range of 100–300 g/cm² at 35° C.

31. The method of claim 29 wherein the body contacting surface of said delivery device has a tack in the range of 100–300 g/cm² at 35° C.

32. The method for testosterone replacement in human males whose testosterone blood levels are below those of normal males which comprises applying a testosterone releasing delivery device to the genitalia of a human male, maintaining said device in testosterone transmitting relationship to the genitalia during an administration period of at least about 8 hours, and delivering testosterone to the male from said delivery device at a varying rate over said administration period, said varying rate being selected to produce testosterone blood levels which approximate the circadian pattern of testosterone blood levels exhibited by a normal male.

33. The method of claim 32 wherein said site for the administration is the scrotum.

34. The method of claim 27 further comprising the steps of removing the used device and replacing it with a fresh device on a daily basis for so long as testosterone replacement is desired.

35. The method of claim 28 further comprising the steps of removing the used device and replacing it with a fresh device on a daily basis for so long as testosterone replacement is desired.

36. The method of claim 29 further comprising the steps of removing the used device and replacing it with a fresh device on a daily basis for so long as testosterone replacement is desired.

37. The method of claim 30 further comprising the steps of removing the used device and replacing it with a fresh device on a daily basis for so long as testosterone replacement is desired.

38. The method of claim 32 further comprising the steps of removing the used device and replacing it with a fresh device on a daily basis for so long as testosterone replacement is desired.

39. The method of claim 33 further comprising the steps of removing the used device and replacing it with a fresh device on a daily basis for so long as testosterone replacement is desired.

* * * * *